United States Patent
Hitt et al.

(10) Patent No.: US 7,333,895 B2
(45) Date of Patent: Feb. 19, 2008

(54) QUALITY ASSURANCE FOR HIGH-THROUGHPUT BIOASSAY METHODS

(75) Inventors: Ben A. Hitt, Gaithersburg, MD (US); Peter J. Levine, Potomac, MD (US); Timothy A. Coleman, Derwood, MD (US)

(73) Assignee: Correlogic Systems, Inc., Rockville, MD (US)

( * ) Notice: Subject to any disclaimer, the term of this patent is extended or adjusted under 35 U.S.C. 154(b) by 425 days.

(21) Appl. No.: 10/628,135

(22) Filed: Jul. 28, 2003

(65) Prior Publication Data

US 2004/0058372 A1 Mar. 25, 2004

Related U.S. Application Data

(60) Provisional application No. 60/398,831, filed on Jul. 29, 2002.

(51) Int. Cl.
*G06F 19/00* (2006.01)
(52) U.S. Cl. ...................................................... 702/19
(58) Field of Classification Search ..................... None
See application file for complete search history.

(56) References Cited

U.S. PATENT DOCUMENTS

| | | | |
|---|---|---|---|
| 3,935,562 A | 1/1976 | Stephens | |
| 4,075,475 A | 2/1978 | Risby et al. | |
| 4,122,343 A | 10/1978 | Risby et al. | |
| 4,122,518 A | 10/1978 | Castleman et al. | |
| 4,697,242 A | 9/1987 | Holland et al. | |
| 4,881,178 A | 11/1989 | Holland et al. | |
| 5,136,686 A | 8/1992 | Koza | |
| 5,210,412 A | 5/1993 | Levis et al. | |
| 5,352,613 A | 10/1994 | Tafas et al. | |
| 5,553,616 A | 9/1996 | Ham et al. | |
| 5,632,957 A | 5/1997 | Heller et al. | |
| 5,649,030 A | 7/1997 | Normile et al. | |
| 5,687,716 A | 11/1997 | Kaufmann et al. | |
| 5,697,369 A | 12/1997 | Long, Jr. et al. | |
| 5,716,825 A | 2/1998 | Hancock et al. | |
| 5,719,060 A | 2/1998 | Hutchens et al. | |
| 5,790,761 A | 8/1998 | Heseltine et al. | |
| 5,825,488 A | 10/1998 | Kohl et al. | |
| 5,839,438 A | 11/1998 | Graettinger et al. | |
| 5,848,177 A | 12/1998 | Bauer et al. | |
| 5,905,258 A | 5/1999 | Clemmer et al. | |
| 5,946,640 A | 8/1999 | Goodacre et al. | |
| 5,974,412 A | 10/1999 | Hazlehurst et al. | |
| 5,989,824 A | 11/1999 | Birmingham et al. | |
| 5,995,645 A | 11/1999 | Soenksen et al. | |
| 6,007,996 A | 12/1999 | McNamara et al. | |
| 6,025,128 A | 2/2000 | Veltri et al. | |
| 6,081,797 A | 6/2000 | Hitt | |
| 6,114,114 A | 9/2000 | Seilhamer et al. | |
| 6,128,608 A | 10/2000 | Barnhill | |
| 6,157,921 A | 12/2000 | Barnhill | |
| 6,225,047 B1 | 5/2001 | Hutchens et al. | |
| 6,295,514 B1 | 9/2001 | Agrafiotis et al. | |
| 6,329,652 B1 | 12/2001 | Windig et al. | |
| 6,427,141 B1 | 7/2002 | Barnhill | |
| 6,493,637 B1 | 12/2002 | Steeg | |
| 6,558,902 B1 | 5/2003 | Hillenkamp | |
| 6,571,227 B1 | 5/2003 | Agrafiotis et al. | |
| 6,579,719 B1 | 6/2003 | Hutchens et al. | |
| 6,615,199 B1 | 9/2003 | Bowman-Amuah | |
| 6,631,333 B1 | 10/2003 | Lewis et al. | |
| 6,675,104 B2 | 1/2004 | Paulse et al. | |
| 6,680,203 B2 | 1/2004 | Dasseux et al. | |
| 6,844,165 B2 | 1/2005 | Hutchens et al. | |
| 6,925,389 B2 | 8/2005 | Hitt et al. | |
| 2002/0046198 A1 | 4/2002 | Hitt | |
| 2002/0138208 A1 | 9/2002 | Paulse et al. | |
| 2002/0193950 A1 | 12/2002 | Gavin et al. | |
| 2003/0004402 A1* | 1/2003 | Hitt et al. | ................... 600/300 |
| 2003/0054367 A1 | 3/2003 | Rich et al. | |
| 2003/0077616 A1 | 4/2003 | Lomas | |

(Continued)

FOREIGN PATENT DOCUMENTS

GB 2 187 035 A 8/1987

(Continued)

OTHER PUBLICATIONS

Olah et al. (Rapid Communications in Mass Spectrometry, vol. 11, pp. 17-23 (1997)).*

(Continued)

*Primary Examiner*—Lori A. Clow
(74) *Attorney, Agent, or Firm*—Cooley Godward Kronish LLP

(57) ABSTRACT

The invention relates to a method of quality assurance/quality control for high-throughput bioassay processes. The method permits monitoring of an entire system for obtaining spectral data from biological samples. Generally, the method includes generating a bioassay process model, comparing a test sample against the bioassay process model. The bioassay process model may be based on the position of a centroid in n-dimensional space. The comparing may include comparing the location of a centroid associated with the test model against the centroid associated with the control model to determine the distance between the two centroids. By generating a trend plot of the distance between the centroid associated with the test sample and the centroid associated with the control model, overall system performance may be monitored over time.

23 Claims, 8 Drawing Sheets

U.S. PATENT DOCUMENTS

| | | |
|---|---|---|
| 2003/0129589 A1 | 7/2003 | Koster et al. |
| 2003/0134304 A1 | 7/2003 | van der Greef et al. |
| 2005/0260671 A1 | 11/2005 | Hitt |
| 2006/0112041 A1 | 5/2006 | Hitt |

FOREIGN PATENT DOCUMENTS

| | | |
|---|---|---|
| RU | 2038598 | 1/1994 |
| WO | WO 93/05478 A1 | 3/1993 |
| WO | WO 97/49989 | 12/1997 |
| WO | WO 99/41612 | 8/1999 |
| WO | WO 99/47925 A2 | 9/1999 |
| WO | WO 99/58972 A1 | 11/1999 |
| WO | WO 00/49410 A3 | 8/2000 |
| WO | WO 00/55628 A1 | 9/2000 |
| WO | WO 01/20043 A1 | 3/2001 |
| WO | WO 01/31579 A2 | 5/2001 |
| WO | WO 01/31580 A2 | 5/2001 |
| WO | WO 01/84140 A2 | 11/2001 |
| WO | WO 02/06829 A2 | 1/2002 |
| WO | WO 02/059822 A2 | 8/2002 |
| WO | WO 02/088744 A2 | 11/2002 |
| WO | WO 03/031031 A1 | 4/2003 |

OTHER PUBLICATIONS

Loging, TW et al., "Identifying Potential Tumor Markers and Antigens by Database Mining and Rapid Expression Screening," Genome Research, 10(9):1393-1402 (Sep. 2000).

Krishnamurthy, T. et al. "Detection of Pathogenic and Non-Pathogenic Bacteria by Matrix-assisted Laser Desorption.Ionization Time-of-flight Mass Spectrometry," Rapid Comms. in Mass Spectrometry, vol. 10, 883-888 (1996).

Adam, B-L et al., "Serum Protein Fingerprinting Coupled with a Pattern-matching Algorithm Distinguishes Prostate Cancer from Benign Hyperplasia and Healthy Men," Cancer Research 62, 3609-3614 (Jul. 1, 2002).

Li, J. et al. "Proteomics and Bioinformatics Approaches for Identification of Serum Biomarkers to Detect Breast Cancer," Clinical Chemistry 48:8, 1296-1304 (2002).

Petricion III, E.F. et al., "Use of proteomic patterns in serum to identify ovarian cancer," The Lancet, vol. 359, 572-577 (Feb. 16, 2002).

Brown, M.P.S. et al. "Knowledge-based analysis of microarray gene expression data by using support vector machines," PNAS vol. 97, No. 1, pp. 262-267 (Jan. 4, 2000).

Kiem, H. & Phuc, D, "Using Rough Genetic and Kohonen's Neural Network for Conceptual Cluster Discovery in Data Mining," New Directions in Rough Sets, Data Mining and Granular-Soft Computing. International Workshop, RSFDGRC Proceedings, pp. 448-452 (Nov. 9, 1999).

Chang, E.I et al., "Using Genetic Algorithms to Select and Create Features for Pattern Classification," IJCNN International Joint Conf. on Neural Networks, pp. III-747 to III-752 (Jan. 8, 1991).

Rosty C. et al., "Identification of Hepatocarcinoma-Intestine-Pancreas/Pancreatitis-associated Protein I as a Biomarker for Pancreatic Ductal Adenocarcinoma by Protein Biochip Technology," Cancer Research 62:1868-75 (Mar. 15, 2002).

Claydon, M.A., "The rapid identification of intact microorganisms using mass spectrometry," Nature Biotech. 14:1584-1586 (Nov. 1996).

Bittl, J.A., "From Confusion to Clarity: Direct Thrombin Inhibitors for Patients with Heparin-Induced Thrombocytopenia," Cath. and Cardio. Interventions 52:473-475 (2001).

Petricoin, E. F. et al., "Clinical Applications of Proteomics," Journal of Nutrition [online], Jul. 2003 [retrieved on Jan. 18, 2005], pp. 1-16, vol. 133, No. 7. Retrieved from the Internet: <URL: http://www.nutrition.org/cgi/content/full/133/7/2476S.

Balteskard, L. et al., "Medical Diagnosis in the Internet Age," The Lancet, Dec. 1999, siv14, vol. 354.

Langdon, W. B., Natural Language Text Classification and Filtering with Trigrams and Evolutionary Nearest Neighbour Classifiers, CWI Report, Jul. 31, 2000, pp. 1-12.

Pictet, O. V. et al., Genetic Algorithms with Collective Sharing for Robust Optimization in Financial Applications, Olsen & Associates, Research Institute for Applied Economics, Jan. 22, 1996, pp. 1-16.

Wu, B. et al., "Comparison of Statistical Methods for Classification of Ovarian Cancer Using Mass Spectrometry Data," Bioinformatics, 2003, pp. 1636-1643, vol. 19, No. 13.

Alaiya, A. A. et al., "Classification of Human Ovarian Tumors Using Multivariate Data Analysis of Polypeptide Expression Patterns," Int. J. Cancer, 2000, pp. 731-736, vol. 86.

Ashfaq, R. et al., "Evaluation of PAPNET™ System for Rescreening of Negative Cervical Smears," Diagnostic Cytopathology, 1995, pp. 31-36, vol. 13, No. 1.

Astion, M. L. et al., "The Application of Backpropagation Neural Networks to Problems in Pathology and Laboratory Medicine," Arch Pathol Lab Med, Oct. 1992, pp. 995-1001, vol. 116.

Atkinson, E. N. et al., "Statistical Techniques for Diagnosing CIN Using Fluorescence Spectroscopy: SVD and CART," Journal of Cellular Biochemistry, 1995, Supplement 23, pp. 125-130.

Babaian, R. J. et al., "Performance of a Neural Network in Detecting Prostate Cancer in the Prostate-Specific Antigen Reflex Range of 2.5 to 4.0 ng/ml,"Urology, 2000, pp. 1000-1006, vol. 56, No. 6.

Bailey-Kellogg, C. et al., "Reducing Mass Degeneracy in SAR by MS by Stable Isotopic Labeling," Journal of Computational Biology, 2001, pp. 19-36, vol. 8, No. 1.

Belic, I. et al., "Neural Network Methodologies for Mass Spectra Recognition," Vacuum, 1997, pp. 633-637, vol. 48, No. 7-9.

Belic, I., "Neural Networks Methodologies for Mass Spectra Recognition," pp. 375-380., additional details unknown, 1995.

Berikov, V. B. et al., "Regression Trees for Analysis of Mutational Spectra in Nucleotide Sequences," Bioinformatics, 1999, pp. 553-562, vol. 15, Nos. 7/8.

Breiman, L. et al., Classification and Regression Trees, Boca Raton, Chapman & Hall/CRC, 1984, pp. 174-265 (Ch. 6, Medical Diagnosis and Prognosis).

Cairns, A. Y. et al., "Towards the Automated Prescreening of Breast X-Rays," Alistair Caims, Department of Mathematics & Computer Science, University of Dundee, pp. 1-5, 1986.

Caprioli, R. M. et al., "Molecular Imaging of Biological Samples: Localization of Peptides and Proteins Using MALDI-TOF MS," Analytical Chemistry, 1997, pp. 4751-4760, vol. 69, No. 23.

Chace, D. H. et al., "Laboratory Integration and Utilization of Tandem Mass Spectrometry in Neonatal Screening: A Model for Clinical Mass Spectrometry in the Next Millennium," Acta Paediatr. Suppl. 432, 1999, pp. 45-47.

Christiaens, B. et al., "Fully Automated Method for the Liquid Chromatographic-Tandem Mass Spectrometric Determination of Cyproterone Acetate in Human Plasma using Restricted Access Material for On-Line Sample Clean-Up", Journal of Chromatography A, 2004, pp. 105-110, vol. 1056.

Chun, J. et al., "Long-term Identification of Streptomycetes Using Pyrolysis Mass Spectrometry and Artificial Neural Networks," Zbl. Bakt., 1997, pp. 258-266, vol. 285, No. 2.

Cicchetti, D. V., "Neural Networks and Diagnosis in the Clinical Laboratory: State of the Art," Clinical Chemistry, 1992, pp. 9-10, vol. 38, No. 1.

Claydon, M. A., et al., "The Rapid Identification of Intact Microorganisms Using Mass Spectrometry," Abstract, 1 page, [online], [retrieved on Feb. 6, 2003]. Retrieved from the internet <URL: http://www.ncbi.nlm.nih.gov/entrez/query.fcgi?cmd=Retrieve&dh=PubMed&list_uids+963...>.

Crawford, L. R. et al. "Computer Methods in Analytical Mass Spectrometry; Empirical Identification of Molecular Class," Analytical Chemistry, Aug. 1968, pp. 1469-1474, vol. 40, No. 10.

Curry, B. et al., "MSnet: A Neural Network That Classifies Mass Spectra," Stanford University, Oct. 1990, To be published in Tetrahedron Computer Methodology, pp. 1-31.

De Brabandere, V. I. et al., Isotope Dilution-Liquid Chromatography/Electrospray Ionization-Tandem Mass Spectrometry for the Determination of Serum Thyroxine as a Potential Reference Method, Rapid Communications in Mass Spectrometry, 1998, pp. 1099-1103, vol. 12.

Dhar, V., et al., Seven Methods for Transforming Corporate Data Into Business Intelligence, Upper Saddle River, N.J., Prentice Hall, 1997, pp. 52-76.

Dudoit, S. et al., "Comparison of Discrimination Methods for the Classification of Tumors using Gene Expression Data," UC Berkeley, Mar. 7, 2000, pp. 1-51, [online], [retrieved on Apr. 4, 2002]. Retrieved from the internet <URL: http://stat-www.berkeley.edu/users/terry/zarray/Html/discr.html>.

Dudoit, S. et al., "Comparison of Discrimination Methods for the Classification of Tumors Using Gene Expression Data," Mathematical Sciences Research Institute, Berkeley, CA, Technical Report # 576, Jun. 2000, pp. 1-43.

Dzeroski, S. et al., "Diterpene Structure Elucidation from 13C NMR-Spectra with Machine Learning," Boston, Kluwer Academic Publishers, Intelligent Data Analysis in Medicine and Pharmacology, 1997, pp. 207-225.

Eghbaldar, A. et al., "Identification of Structural Features from Mass Spectrometry Using a Neural Network Approach: Application to Trimethylsilyl Derivatives Used for Medical Diagnosis," J. Chem. Inf. Comput. Sci., 1996, pp. 637-643, vol. 36, No. 4.

Freeman, R. et al., "Resolution of Batch Variations in Pyrolysis Mass Spectrometry of Bacteria by the Use of Artificial Neural Network Analysis," Antonie van Leeuwenhoek, 1995, pp. 253-260, vol. 68.

Furlong, J. W. et al., "Neural Network Analysis of Serial Cardia Enzyme Data; A Clinical Application of Artificial Machine Intelligence," American Journal of Clinical Pathology, Jul. 1991, pp. 134-141, vol. 96, No. 1.

Gaskell, S. J., "Electrospray: Principles and Practice," Journal of Mass Spectrometry, 1997, pp. 677-688, vol. 32.

George, S. E., "A Visualization and Design Tool (AVID) for Data Mining with the Self-Organizing Feature Map," International Journal on Artificial Intelligence Tools, 2000, pp. 369-375, vol. 9, No. 3.

Goodacre, R. et al. "Rapid Identification of Urinary Tract Infection Bacteria Using Hyperspectral Whole-Organism Fingerprinting and Artificial Neural Networks.," Microbiology, 1998, pp. 1157-1170, vol. 144.

Goodacre, R. et al., "Correction of Mass Spectral Drift Using Artificial Neural Networks," Analytical Chemistry, 1996, pp. 271-280, vol. 68.

Goodacre, R. et al., "Discrimination between Methicillin-Resistant and Methicillin-Susceptible *Staphylococcus aureus* Using Pyrolysis Mass Spectrometry and Artificial Neural Networks," Journal of Antimicrobial Chemotherapy, 1998, pp. 27-34, vol. 41.

Goodacre, R. et al., "Identification and Discrimination of Oral *Asaccharolytic eubacterium* spp. by Pyrolysis Mass Spectrometry and Artificial Neural Networks," Current Microbiology, 1996, pp. 77-84. vol. 32.

Goodacre, R. et al., "Quantitative Analysis of Multivariate Data Using Artificial Neural Networks: A Tutorial Review and Applications to the Deconvolution of Pyrolysis Mass Spectra," Zbl. Bakt., 1996, pp. 516-539, vol. 284.

Goodacre, R. et al., "Sub-species Discrimination, Using Pyrolysis Mass Spectrometry and Self-organising Neural Networks, of Propionibacterium acnes Isolated from Normal Human Skin," Zbl. Bakt., 1996, pp. 501-515, vol. 284.

Gray, N. A. B., "Constraints on 'Learning Machine' Classification Methods," Analytical Chemistry, Dec. 1976, pp. 2265-2268, vol. 48, No. 14.

Hackett, P. S. et al., "Rapid SELD1 Biomarker Protein Profiling of Serum from Normal and Prostate Cancer Patients," American Association for Cancer Research (abstract only), Mar. 2000, pp. 563-564, vol. 41.

Halket, J. M. et al., "Deconvolution Gas Chromatography/Mass Spectrometry of Urinary Organic Acids—Potential for Pattern Recognition and Automated Identification of Metabolic Disorders," Rapid Communications in Mass Spectrometry, 1999, pp. 279-284, vol. 13.

Hashemi, R. R. et al., "Identifying and Testing of Signatures for Non-Volatile Biomolecules Using Tandem Mass Spectra," SIGBIO Newsletter, Dec. 1995, pp. 11-19, vol. 15, No. 3.

Hausen, A. et al., "Determination of Neopterine in Human Urine by Reversed-Phase High-Performance Liquid Chromatography," Journal of Chromatography, 1982, pp. 61-70, vol. 227.

Hess, K. R. et al., "Classification and Regression Tree Analysis of 1000 Consecutive Patients with Unknown Primary Carcinoma," Clinical Cancer Research, Nov. 1999, pp. 3403-3410, vol. 5.

Jain, A. K. et al., "Statistical Pattern Recognition: A Review," IEEE Transactions On Pattern Analysis and Machine Intelligence, Jan. 2000, pp. 4-37, vol. 22, No. 1.

Jellum, E. et al., "Mass Spectrometry in Diagnosis of Metabolic Disorders," Biomedical and Environmental Mass Spectrometry, 1988, pp. 57-62, vol. 16.

Jurs, P. C. et al., "Computerized Learning Machines Applied to Chemical Problems; Molecular Formula Determination from Low Resolution Mass Spectrometry," Analytical Chemistry, Jan. 1969, pp. 21-27, vol. 41, No. 1.

Kenyon, R. G. W. et al., "Application of Neural Networks to the Analysis of Pyrolysis Mass Spectra," Zbl. Bakt., 1997, pp. 267-277, vol. 285.

Kohavi, R. et al., "Wrappers for Feature Subset Selection," Artificial Intelligence, 1997, pp. 273-324, vol. 97.

Kohno, H. et al., "Quantitative Analysis of Scintiscan Matrices by Computer," Japanese Journal of Medical Electronics and Biological Engineering, Aug. 1974, pp. 22-29, English Abstract.

Lewis, R. J., "An Introduction to Classification and Regression Tree (CART) Analysis," presented at 2000 Annual Meeting of the Society for Academic Emergency Medicine in San Francisco, California, 2000, pp. 1-14.

Liotta, L. et al., "Molecular Profiling of Human Cancer," Nature Genetics, Oct. 2000, pp. 48-56, vol. 1.

Lockhart, D. J. et al., "Genomics, Gene Expression and DNA Arrays," Nature, Jun. 2000, pp. 827-836, vol. 405.

Lowry, S. R. et al., "Comparison of Various K-Nearest Neighbor Voting Schemes with the Self-Training Interpretive and Retrieval System for Identifying Molecular Substructures from Mass Spectral Data," Analytical Chemistry, Oct. 1977, pp. 1720-1722, vol. 49, No. 12.

Luo, Y. et al., Quantification and Confirmation of Flunixin in Equine Plasma by Liquid Chromatograph—Quadrupole Time-Of-Flight Tandem Mass Spectrometry, Journal of Chromatography B, 2004, pp. 173-184, vol. 801.

Macfie, H. J. H. et al., "Use of Canonical Variates Analysis in Differentiation of Bacteria by Pyrolysis Gas-Liquid Chromatography," Journal of General Microbiology, 1978, pp. 67-74, vol. 104.

Malins, D. C. et al., "Models of DNA Structure Achieve Almost Perfect Discrimination Between Normal Prostate, Benign Prostatic Hyperplasia (BPH), and Adenocarcinoma and Have a High Potential for Predicting BPH and Prostrate Cancer," Proceedings of the National Academy of Sciences, Jan. 1997, pp. 259-264, vol. 94.

Marvin, L. F. et al., "Characterization of a Novel Sepia Officinalis Neuropeptide using MALDI-TOL MS and Post-Source Decay Analysis," Peptides, 2001, pp. 1391-1396, vol. 22.

Meuzelaar, H. L. C. et al., "A Technique for Fast and Reproducible Fingerprinting of Bacteria by Pyrolysis Mass Spectrometry," Analytical Chemistry, Mar. 1973, pp. 587-590, vol 45, No. 3.

Meyer, B. et al., "Identification of the 1H-NMR Spectra of Complex Oligosaccharides with Artificial Neural Networks," Science, Feb. 1991, pp. 542-544, vol. 251.

Microsoft Press, Computer Dictionary, Second Edition, The Comprehensive Standard for Business, School, Library, and Home, Microsoft Press, Redmond, WA, 1994, pp. 87 and 408.

Moler, E. J. et al., "Analysis of Molecular Profile Data Using Generative and Discriminative Methods,", Physiol. Genomics, Dec. 2000, pp. 109-126, vol. 4.

Nikulin, A. E. et al., "Near-Optimal Region Selection for Feature Space Reduction: Novel Preprocessing Methods for Classifying MR Spectra," NMR Biomedicine, 1998, pp. 209-216, vol. 11.

Nilsson, T. et al., "Classification of Species in the Genus *Penicillium* by Curie Point Pyrolysis/Mass Spectrometry Followed by Multivariate Analysis and Artificial Neural Networks," Journal of Mass Spectrometry, 1996, pp. 1422-1428, vol. 31.

Oh, J. M. C. et al., "A Database of Protein Expression in Lung Cancer," Proteomics, 2001, pp. 1303-1319, vol. 1.

Pei, M. et al. "Feature Extraction Using Genetic Algorithms," Proceedings of the 1st International Symposium on Intelligent Data Engineering and Learning, IDEAL '98, Oct. 1998, pp. 371-384, Springer, Hong Kong.

Petricoin, E. F., III et al., "Serum Proteomic Patterns for Detection of Prostate Cancer," Journal of the National Cancer Institute, Oct. 16, 2002, pp. 1576-1578, vol. 94, No. 20.

Prior, C. et al., "Potential of Urinary Neopterin Excretion in Differentiating Chronic Non-A, Non-B Hepatitis from Fatty Liver,"0 The Lancet, Nov. 28, 1987, pp. 1235-1237.

Reed, J. "Trends in Commercial Bioinformatics," Oscar Gruss Biotechnology Review, Mar. 2000, pp. 1-20.

Reibnegger, G. et al., "Neural Networks as a Tool for Utilizing Laboratory Information: Comparison with Linear Discriminant Analysis with Classification and Regression Trees," Proceedings of the National Academy of Sciences, Dec. 1991, pp. 11426-11430, vol. 88.

Ricketts, I. W. et al., "Towards the Automated Prescreening of Cervical Smears," Mar. 11, 1992, Applications of Image Processing in Mass Health Screening, IEE Colloquium, pp. 1-4.

Roses, A.D., "Pharmacogenetics and the Practice of Medice," Nature, Jun. 15, 2000, pp. 857-865, vol. 405.

Salford Systems, "Salford Systems White Paper Series," pp. 1-17 [online], [retrieved on Oct. 17, 2000], Retrieved from the internet: <URL: http//www.salford-systems.com/whitepaper.html>.

Schroll, G. et al., "Applications of Artificial Intelligence for Chemical Inference, III. Aliphatic Ethers Diagnosed by Their Low-Resolution Mass Spectra and Nuclear Magnetic Resonance Data," Journal of the American Chemical Society, Dec. 17, 1969, pp. 7440-7445.

Shaw, R. A. et al., "Infrared Spectroscopy of Exfoliated Cervical Cell Specimens," Analytical and Quantitative Cytology and Histology, Aug. 1999, pp. 292-302, vol. 21, No. 4.

Shevchenko, A. et al., "MALDI Quadupole Time-of-Flight Mass Spectrometry: A Powerful Tool for Proteomic Research," Analytical Chemistry, May 1, 2000, pp. 2132-2141, vol. 72, No. 9.

Strouthopoulos, C. et al. "PLA Using RLSA and a Neural Network," Engineering Applications of Artificial Intelligence, 1999, pp. 119-138, vol. 12.

Taylor, J. et. al., "The Deconvolution of Pyrolysis Mass Spectra Using Genetic Programming: Application to the Identification of Some Eubacterium Species," FEMS Microbiology Letters, 1998, pp. 237-246, vol. 160.

Tong, C. S. et al., "Mass Spectral Search method using the Neural Network approach," International Joint Conference on Neural Networks, Washington, DC Jul. 10-16, 1999, Proceedings, vol. 6 of 6, pp. 3962-3967.

Tong, C. S. et al., "Mass spectral search method using the neural network approach," Chemometrics and Intelligent Laboratory Systems, 1999, pp. 135-150, vol. 49.

Von Eggeling, F. et al, "Mass Spectrometry Meets Chip Technology: A New Proteomic Tool in Cancer Research?," Electrophoresis, 2001, pp. 2898-2902, vol. 22, No. 14.

Voorhees, K. J. et al., "Approaches to Pyrolysis/Mass Spectrometry Data Analysis of Biological Materials," in: Meuzelaar, H. L. C., Computer-Enhanced Analytical Spectroscopy, vol. 2, New York, Plenum Press, 1990, pp. 259-275.

Werther, W. et al., "Classification of Mass Spectra; a Comparison of Yes/No Classification Methods for the Recognition of Simple Structural Properties," Chemometrics and Intelligent Laboratory Systems, 1994, pp. 63-76, vol. 22.

Wythoff, B. J. et al., "Spectral Peak Verification and Recognition Using a Multilayered Neural Network," Analytical Chemistry, Dec. 15, 1990, pp. 2702-2709, vol. 62, No. 24.

Xiao, Z. et al., Quantitation of Serum Prostate-Specific Membrane Antigen by a Novel Protein Biochip Immunoassay Discriminates Benign from Malignant Prostate Disease, Cancer Research, Aug. 15, 2001, pp. 6029-6033, vol. 61.

Yao, X. et al. "Evolving Artificial Neural Networks for Medical Applications," Proceedings of the First Korea-Australia Joint Workshop on Evolutionary Computation, Sep. 1995, pp. 1-16.

Yates, J. R. III, "Mass Spectrometry and the Age of the Proteome," Journal of Mass Spectrometry, 1998, pp. 1-19, vol. 33.

Zhang, Z. "Combining Multiple Biomarkers in Clinical Diagnostics—A Review of Methods and Issues," Center for Biomarker Discovery, Department of Pathology, Johns Hopkins Medical Institutions, 14 pages, 2001.

Zhang, Z. et al., "Proteomics and Bioinformatics Approaches for Identification of Serum Biomarkers to Detect Breast Cancer," Clinical Chemistry, 2002, pp. 1296-1304, vol. 48, No. 8.

Paweletz, C. P., "Rapid Protein Display Profiling of Cancer Progression Directly from Human Tissue Using a Protein Biochip," Drug Development Research 49:34-42 (2000).

Ciphergen European Update, 1:1-4 (2001).

Kohonen, T. Self Organizing Maps (Springer 2001), pp. 1-70.

Jun Zhang, *Dynamics and Formation of Self-Organizing Maps, in* "Self-Organizing Map Formation: Foundations of Neural Computation," pp. 55-67 (Klaus Obermayer & Terrence J. Sejnowski eds.), 2001.

Kohonen, T. "Self-Organization and Associative Memory" (Springer 1988), pp. 30-67.

Holland, J.H., "Adaption in Natural and Artificial Systems: An Introductory Analysis with Applications to Biology, Control, and Artificial Intelligence" (MIT Press 2001), pp. 1-31; 89-120.

* cited by examiner

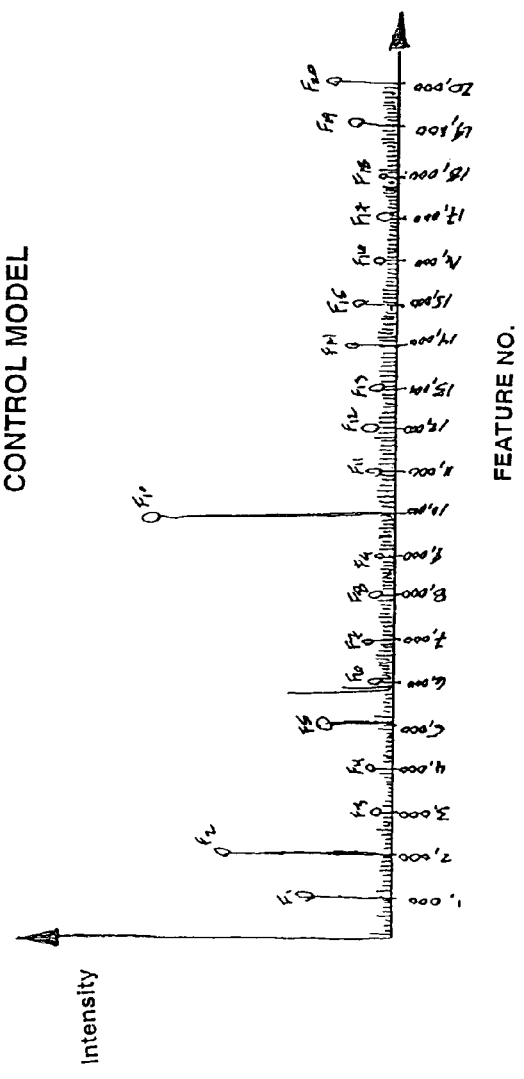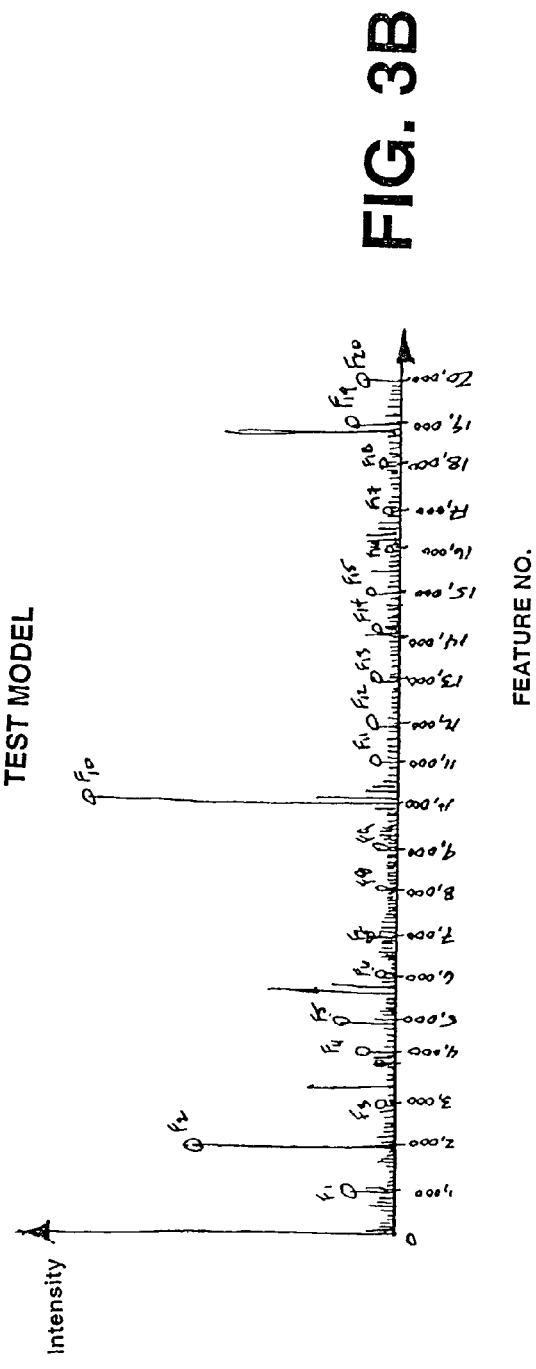

QUALITY ASSURANCE FOR HIGH-THROUGHPUT BIOASSAY METHODS

CROSS-REFERENCE TO RELATED APPLICATIONS

This application claims priority under 35 U.S.C. § 119(e) to U.S. Provisional Patent Application No. 60/398,831, entitled "Quality Assurance/Quality Control for SELDI-TOF Mass Spectra," filed on Jul. 29, 2002, the contents of which are hereby incorporated by reference in their entirety.

STATEMENT OF FEDERALLY SPONSORED RESEARCH

The research performed in connection with some of the subject matter disclosed in this application was performed on samples supplied by the United States Government.

BACKGROUND OF THE INVENTION

The invention relates generally to the field of bioinformatics. More specifically, the invention relates to a method of quality control for bioinformatic systems.

Methods of analyzing biological samples are generally known. In a typical analysis, mass spectroscopy is performed on the biological sample to determine its overall biochemical make-up. Based on the mass spectra obtained from the mass spectroscopy, various diagnostics may be run.

When biological samples are analyzed, it is desirable to perform more than one trial on the biological sample, thereby improving the accuracy of the diagnostic. Analysis of biological samples may be performed by using biochips, electrospray, or other protein separation techniques. A problem arises as samples are analyzed over time. The apparatus used to extract data from the samples may become uncalibrated, or a variation between chips when using biochips (e.g., in using SELDI or MALDI methods), or between diluents (when using electrospray techniques) may cause data obtained from the sample to become skewed.

Therefore, there is a need for a method of monitoring bioassay processes to determine when the process may be producing inaccurate data that may lead to a misdiagnosis.

SUMMARY OF THE INVENTION

The invention provides a quality control method for ensuring that a particular bioassay process is yielding acceptable data. Using the methods of the invention, the reliability of data used in a diagnostic procedure may be improved. Another embodiment of the invention includes using the Knowledge Discovery Engine ("KDE") to classify and archive biochips and to distinguish between type of biochips. Alternatively, the KDE may be used to classify and archive diluents and distinguish between diluents having different composition or concentrations.

The invention may use the KDE to identify hidden patterns across a wide variety of serum samples and biochips to generate a control model. Alternatively, the KDE does not have to be used to perform the methods of the invention.

The KDE is disclosed in U.S. patent application Ser. No. 09/883,196, now U.S. Pat. No. 7,096,206, entitled "Heuristic Methods of Classification," filed Jun. 19, 2001 ("Heuristic Methods"), and U.S. patent application Ser. No. 09/906,661, now U.S. Pat. No. 6,925,389 entitled "A Process for Discriminating Between Biological States Based on Hidden Patterns from Biological Data," filed Jul. 18, 2001 ("Hidden Patterns"), the contents of both of which are hereby incorporated by reference in their entirety. Soft-ware running the KDE is available from Correlogic Systems, Inc. under the name Proteome Quest™.

As described above, the KDE does not need to be used to practice the invention. One method of practicing the invention includes defining a number of features characteristic of the control sample. As used herein the term "feature" refers to a particular mass to charge ratio (m/z) within a spectrum. Additionally, as used herein, the term "vector" refers to a feature having a particular magnitude. Therefore, a vector is a two-dimensional value having both a mass to charge value and a magnitude.

After the features are defined, the vectors are plotted in n-dimensional space, where n is the number of defined features. The plotted vectors will define a centroid. A centroid is a reference point located in n-dimensional space and associated with the selected features. This centroid is the control centroid.

Using a preserved aliquot of the same mixture used to generate the model, the spectral information from the aliquot of molecular mixture is obtained using the bioassay process. The vectors associated with the predetermined features selected in the generation of the control model are mapped in n-dimensional space. Using these newly mapped vectors, a comparison can be made of the deviation of a test centroid based on the newly mapped vectors from the control centroid associated with the control model.

When a determination is made that the test centroid deviates too far from the control centroid, calibration of the apparatus, a change of equipment, or other system adjustment may be needed. For example, if a general trend away from the control centroid is noticed, this will indicate that the mass spectrometer or other analyzer is uncalibrated or may need repair. A sudden shift in the data away from the control centroid may mean a number of things. First, it may mean that diluents or other preparation reagents were bad. In this case, a new diluent or reagent should be mixed. Additionally, a sudden shift could indicate that the type of biochip being used as a protein separation method has been changed. Alternatively, a sudden shift in the data away from the control centroid may indicate that the apparatus settings have changed, and the apparatus should be recalibrated.

BRIEF DESCRIPTION OF THE DRAWINGS

FIGS. 3A and 3B are exemplary spectra obtained using the methods of the invention.

DETAILED DESCRIPTION

Generally, the invention includes a method of obtaining a control model for use in a bioinformatics system and a method for quality assurance in a bioassay process. Another embodiment of the invention may be used to distinguish between different types of biochips or diluents used in electrospray processes.

Figure 1:
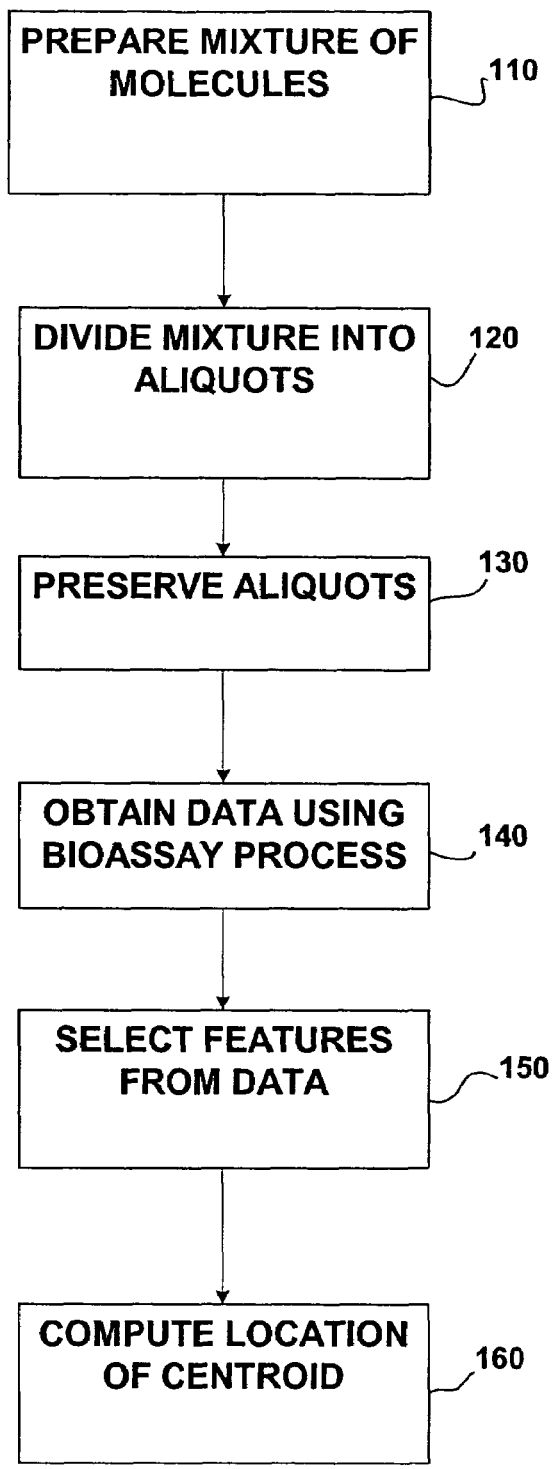
FIG. 1 is a flow chart of a method of obtaining a control model according to one aspect of the invention.

A method of obtaining a control model according to an aspect of the invention is illustrated generally in FIG. 1. A mixture of molecules is prepared in a step 110. The mixture of molecules can include any mixture of molecules. The mixture of molecules may include any natural or artificial molecules. The molecules may have an atomic weight of greater than 400 and be water soluble. In one embodiment, the mixture of molecules can include a mixture of isolated peptides.

After the mixture of molecules is prepared, the mixture is divided into aliquots at a step 120. Enough aliquots may be made so as to permit continued use over a desired number of tests, which may be over a period of years. The aliquoted mixture may be used for comparison purposes after generation of the control model.

Once the mixture is divided into aliquots, all of the aliquots are preserved in step 130. In one embodiment, this includes freezing the mixture in liquid nitrogen. To enhance the consistency of the results, it is desirable to freeze all of the aliquots of the mixture so that any change that the mixture may undergo due to the freezing or thawing process is constant across all aliquots.

Next, to obtain data using a bioassay process, some aliquots of the mixture are thawed. The aliquots may be thawed at room temperature. Once the mixture has thawed, the mixture may be placed in a ice bath at about 4° C. Although it is not critical that the mixture be kept at 4° C., it is advantageous because most biological samples have a high degree of stability around this temperature.

In one embodiment of the invention, the molecular mixture is then analyzed using mass spectrometry, and a data set based on the mass spectrometry is obtained at a step 140.

In an embodiment where the KDE is not used, a selection of features may be made from the mass spectrometry data at step 150. For example, every thousandth feature may be selected, as illustrated in FIG. 3A. Once the features are selected, these features are fixed, i.e., these will be the features that will be observed for all test samples. Any number of features may be selected, for example, every tenth feature, every hundredth feature, or every thousandth feature. The features chosen may be completely random as well, as long as the same features are observed and compared against the control model during testing.

Once the features are chosen, vectors based on these features are mapped into n-dimensional space, where "n" corresponds to the number of features selected, to define a centroid in that space at step 160. The vectors have mass to charge values representing the selected features, and have a magnitude. The location of the centroid may define the control model. This centroid may act as the basis for comparison for the test spectra.

Any number of aliquots of the mixture may be analyzed to generate the control model. Preferably, more than one aliquot of the mixture is analyzed. The greater the number of aliquots analyzed, the more robust the model will be. When analyzing multiple aliquots, the features observed should always be the same features (e.g., every thousandth feature). This is illustrated in FIG. 3B. FIGS. 3A and 3B are examples of mass spectra outputs from a hypothetical molecular mixture. One mass spectrum that was used to generate the control model is shown in FIG. 3A. Every thousandth feature has been selected, yielding a total of 20 features ($F_1$-$F_{20}$).

An exemplary test sample is shown in FIG. 3B, having the same features selected (i.e., every thousandth feature is selected). While substantially the same, the spectrum illustrated in FIG. 3A is different from that illustrated in FIG. 3B in that some of the peaks have a different magnitude. For example, peak $F_{10}$ has a slightly greater magnitude in FIG. 3B. Peaks $F_1$, $F_{14}$, and $F_{20}$ have smaller magnitudes in FIG. 3B than those shown in FIG. 3A. These varied magnitudes will impact the location of the vector associated with that feature in n-dimensional space. By producing features with different magnitudes (i.e., a vector), the centroid based on those features will be displaced with respect to the control centroid.

Figure 2:
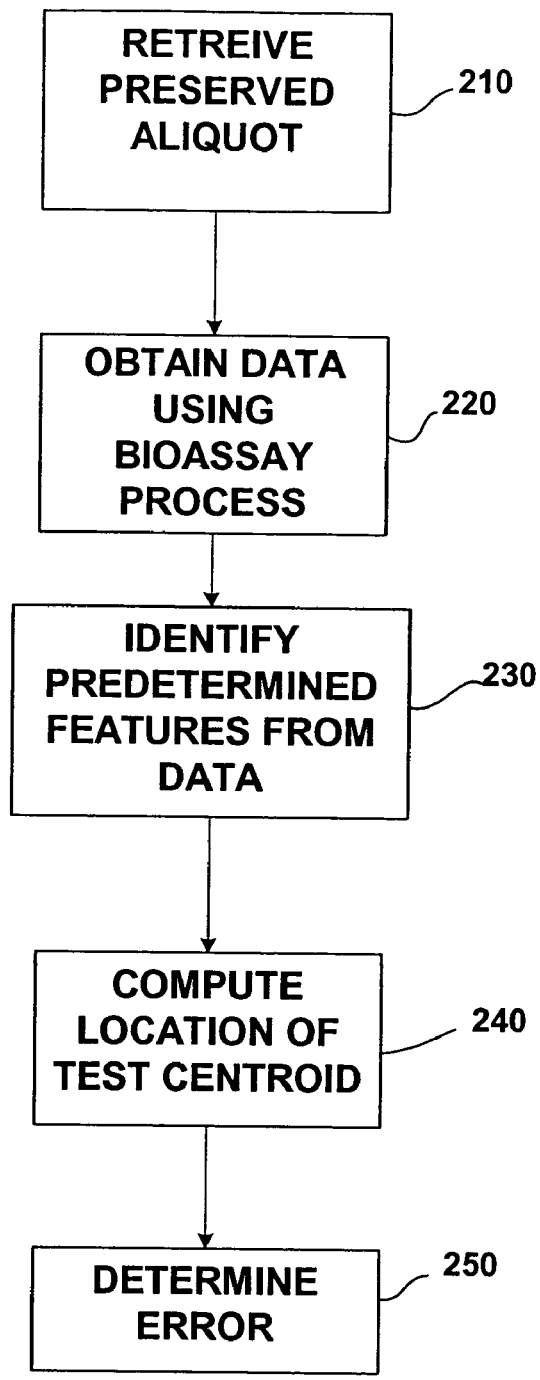
FIG. 2 shows a method of testing a system against the control model to determine an error in the control model.

A method of using the control model for quality assurance/quality control according to an aspect of the invention is illustrated generally in FIG. 2. Once the control model is generated, spectra may be compared against the control model to determine if the system, the biochip, or the diluents being used are yielding precise results.

To run a diagnostic on the system, an aliquot of the initial molecular mixture may be retrieved and thawed in a step 210. The thawing process should replicate the thawing process used for generating the control model. For example, if the aliquots used for making the control model were thawed at room temperature, then the aliquot used to run the test model should be thawed at room temperature. If the aliquots used to generate the control model were then placed in an ice bath at 4° C., then the aliquot for the test model may be placed in an ice bath at 4° C. The consistency in retrieval methods may enhance precision and prevent errors that may be generated by different preservation and retrieval methods.

Then, using the same bioassay process used to obtain the control model, spectral data may be obtained for the mixture in a step 220. To achieve a basis for comparison, the same features should be identified in the test spectrum. Vectors associated with these features may be mapped in n-dimensional space. The set of vectors obtained from this mapping will define a test centroid in step 240. The test centroid may then be used to determine the degree of error between the test spectrum and the control spectrum in a step 250.

Error may be determined by calculating a distance between the fixed control centroid and the test centroid. The distance may be calculated in n-dimensional space as described in further detail below. An acceptable degree of error may be one to two standard deviations. The standard deviation is calculated based on the vectors used to develop the control centroid. If the test centroid is greater than a predetermined distance from the control centroid, a problem may exist in the apparatus used to conduct the bioassay process (e.g., the biochip surfaces, the electrospray apparatus) or the diluents used (with respect to the electrospray processes).

Figure 4:
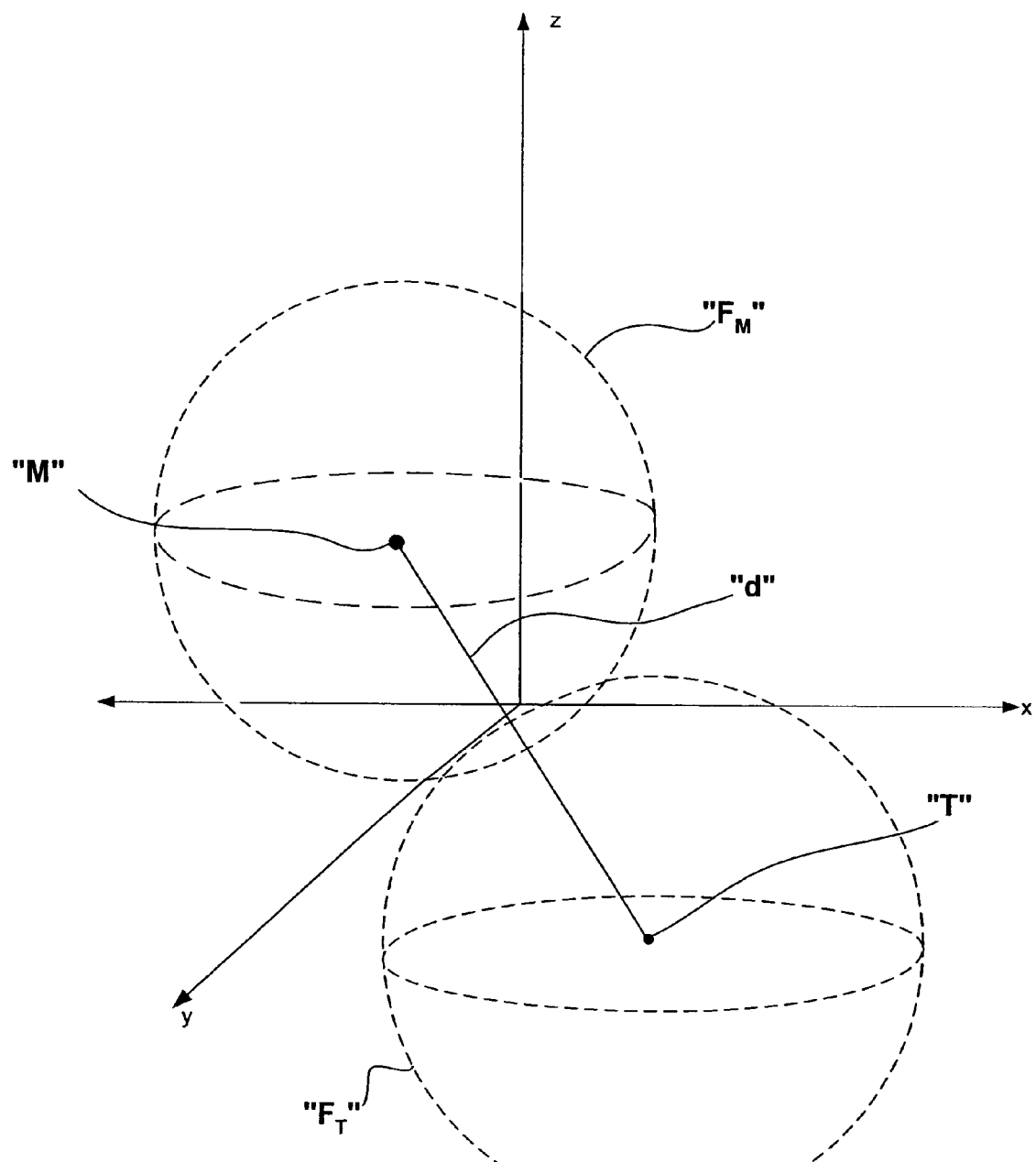
FIG. 4 illustrates an example of comparing a test centroid to a control centroid according to one embodiment of the invention.

A method of determining the error according to an aspect of the invention is shown generally in FIG. 4. While the plot shown in FIG. 4 is depicted in three dimensions, it should be understood that a plot obtained by using the methods of the invention could be in any number of dimensions. A three-dimensional model is illustrated because it is easily conceptualized.

FIG. 4 depicts a first sphere in three-dimensional space, $F_M$. Sphere $F_M$ contains a set of all vectors corresponding to the selected features. This concept could be conceptualized as a sphere containing (on its surface and/or in its interior)

a multitude of points. The plotted vectors need not be homogeneously distributed thought the sphere (or in n-dimensional space the hypersphere or other hyper-volume). The plotted vectors may be averaged to a centroid, "M." The centroid will be located at the center of the sphere. The centroid "M" is the control model centroid, and will serve as the basis of comparison for test centroids.

When a test spectrum is obtained, the test spectrum may also be plotted. The vectors for a single spectrum would plot to a single point in the illustrated space. Vectors for multiple spectra would plot to a point for each spectrum. The plotting of multiple spectra is again, for ease of conceptualization, illustrated in FIG. 4 as a sphere, $F_T$, but one of skill in the art will understand that the number of dimensions will be dependent on the number of features selected in generating the control model. Sphere $F_T$ is centered on a test centroid, designated as "T." As can be seen in FIG. 4, the spheres defining the features are offset, in that their centroids are not colocated at the same point in the space. If the spheres were centered on the same point, then one would know that the test model was identical with the control model. In some instances, this may not be the case. Many times, the test centroid, "T" will be displaced from the control model centroid, "M." This displacement is an indicator of the status of the bioassay process as a whole. The displacement between the two centroids is illustrated generally as "d." In three dimensional space, "d" may be determined using the following three-dimensional formula for the distance between the two centroids in FIG. 4 is:

$$d=|M(x,y,z)T(a,b,c)|=\sqrt{(x-a)^2+(y-b)^2+(z-c)^2}.$$

When expanding this to n-dimensional space, the distance between the two points is given by:

$$d = |M(m_1, m_2, \ldots, m_n)T(t_1, t_2, \ldots, t_n)| = \sqrt{\sum_{i=1}^{n} (m_i - q_i)^2}.$$

If the distance between points "M" and "T" are greater than a predetermined tolerance, then calibration or other system changes may be needed (e.g., new diluents may need to be used, new biochips etc.). If the distance between points "M" and "T" are equal to or within the predetermined tolerances, then samples may be evaluated using the high-throughput bioassay process.

Applying the method of the invention to an electrospray system requires only a few modifications to the method as applied to biochip technology. For example, in generating the control model, as illustrated in FIG. 1, step 140 would include obtaining data using an electrospray process for protein separation (rather than using biochips). The remaining steps are substantively unchanged.

The invention may be used to monitor the performance of an overall system, and depending on the behavior of the test model with respect to the control model, one may determine whether a particular aspect of the system is producing unreliable results.

Figure 7:
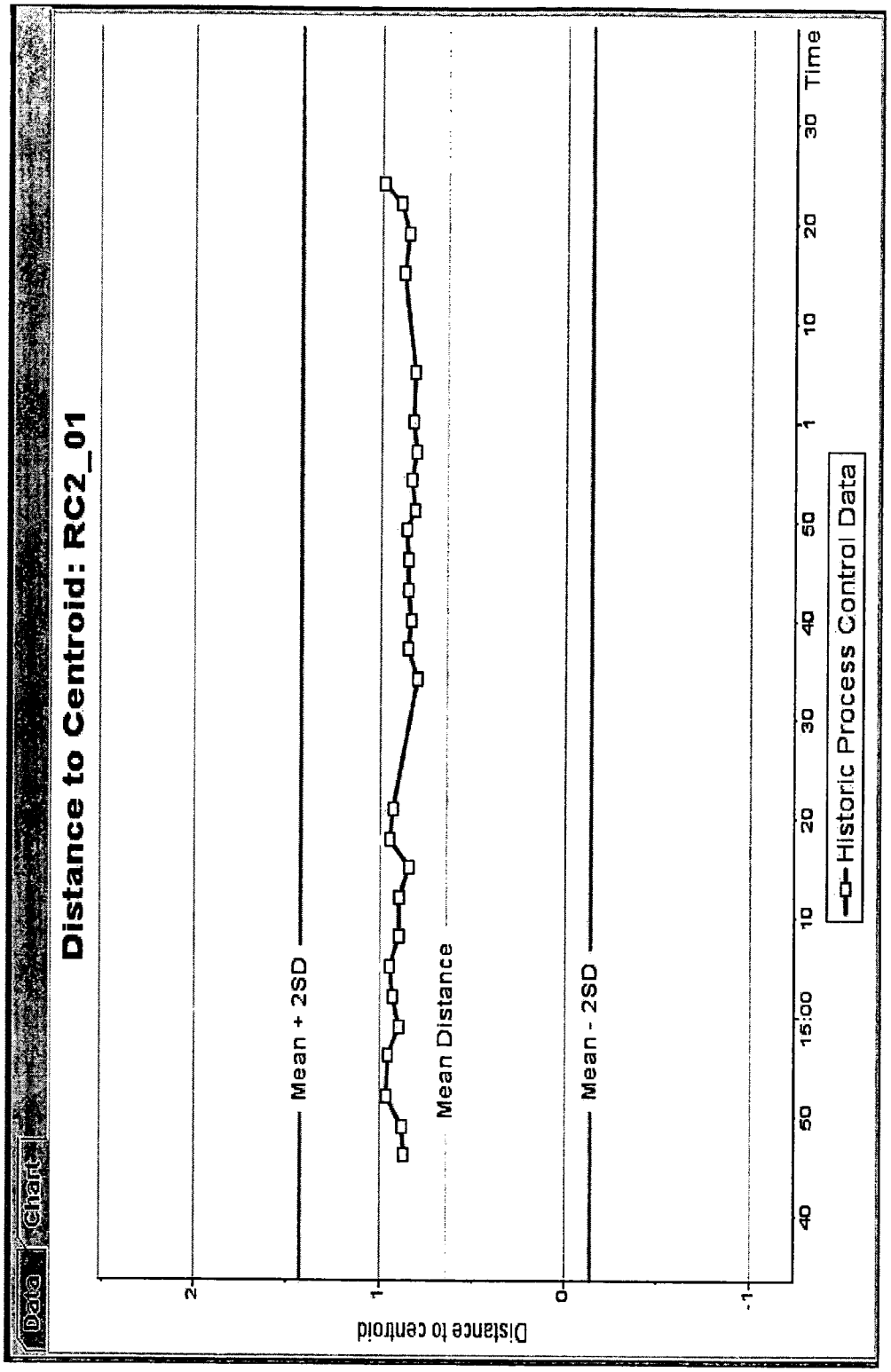
FIG. 7. is a trend plot illustrating the performance of an electrospray system when compared with a predetermined model.
Figure 8:
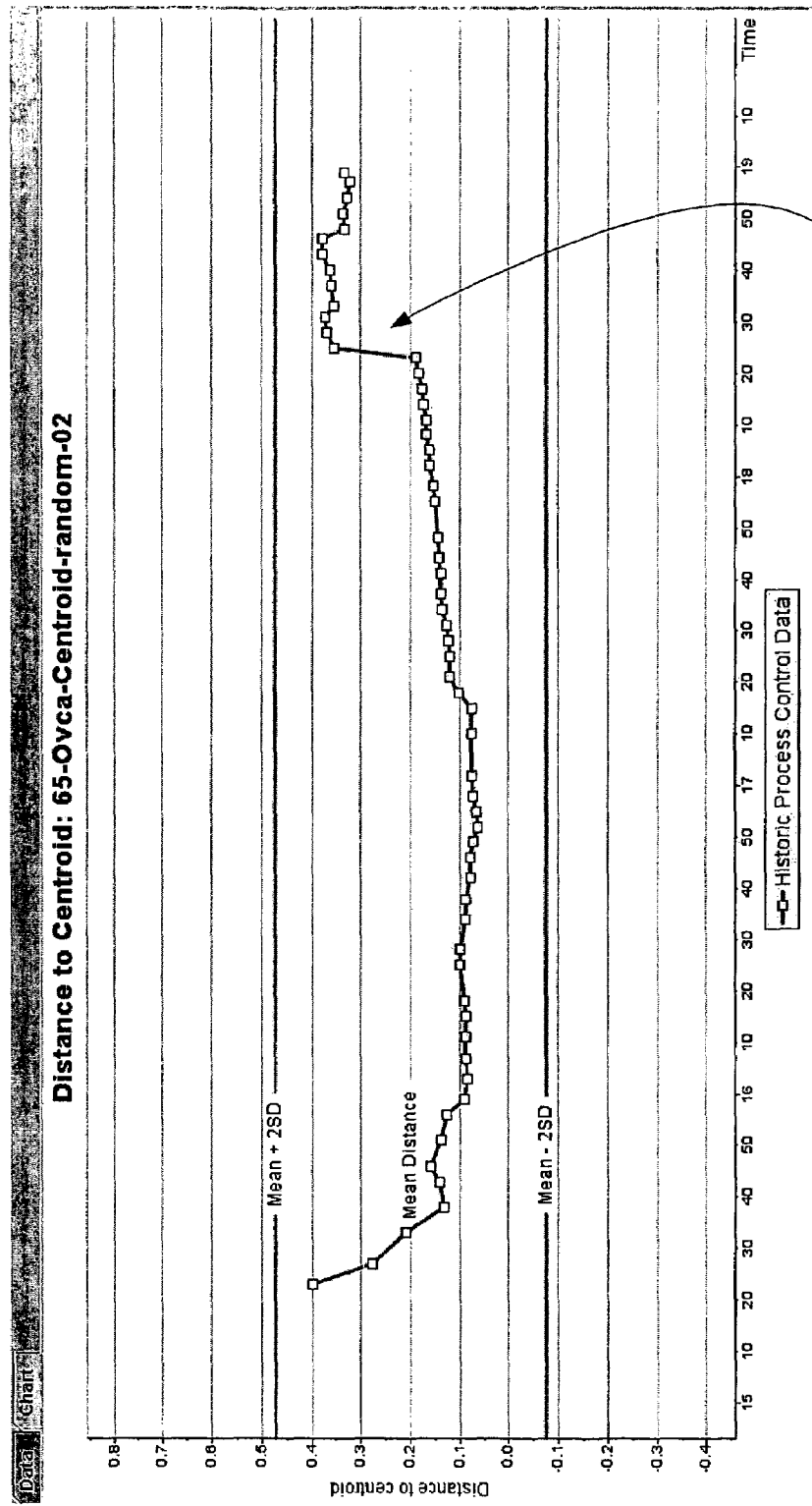
FIG. 8 is a trend plot illustrating the performance of a SELDI system utilizing biochips when compared to a biochip control model.

One method of monitoring system performance is to generate a plot of the distance of the test centroid to the control centroid, using data taken over time. Exemplary plots are illustrated in FIGS. 7 and 8. Monitoring these plots will allow overall system performance to be monitored. Furthermore, interpreting these plots will enable one to understand where problems may be arising that affect the quality of the system.

For example, if a general trend away from the control centroid is noticed, this will indicate that the mass spectrometer or other analyzer is uncalibrated, and may need repair. A sudden shift in the data away from the control centroid may mean a number of things. First, it may mean that diluents or other preparation reagents were bad. In this case, a new reagent should be mixed. Alternatively, a sudden shift in the data away from the control centroid may indicate that the apparatus settings have changed, and the apparatus should be recalibrated.

FIG. 7 illustrates a trend plot for monitoring an electrospray system. This plot illustrates a consistent system behavior. If anything, this plot illustrates that the system is settling in over time, thereby producing more consistent results. Here, the data is falling within one standard deviation of the mean, the mean being based on the mean distance of a vector in the control model from the control centroid.

FIG. 8 illustrates a trend plot for monitoring a SELDI system. The jump in the distance to centroid illustrated in FIG. 8 indicates a position where a new type of biochip was being used in the system. While this biochip performed within two standard deviations of the mean, it performed comparatively worse than the first biochip when being compared to the control model. The overall jump in the trend plot is due to the different chip surfaces which will produce different vectors in the test model. Because the different chip surface produces different vectors in the test model, the test centroid begins to drift away from the control model. In one embodiment of the invention, if the test centroid falls outside of two standard deviations from the mean, the system is deemed unsuitable. In another embodiment, the tolerances could be more strict, and the system may be deemed unsuitable if the test centroid was more than one standard deviation from the mean.

The methods of the invention may, in a particular application, be employed to determine if biochip surfaces are of a particular type and determined if the biochips are acceptable for use in medical diagnostics. Furthermore, the KDE may be used to discover features that are only salient to different chip surfaces or different diluents used for electrospray systems.

Figure 5:
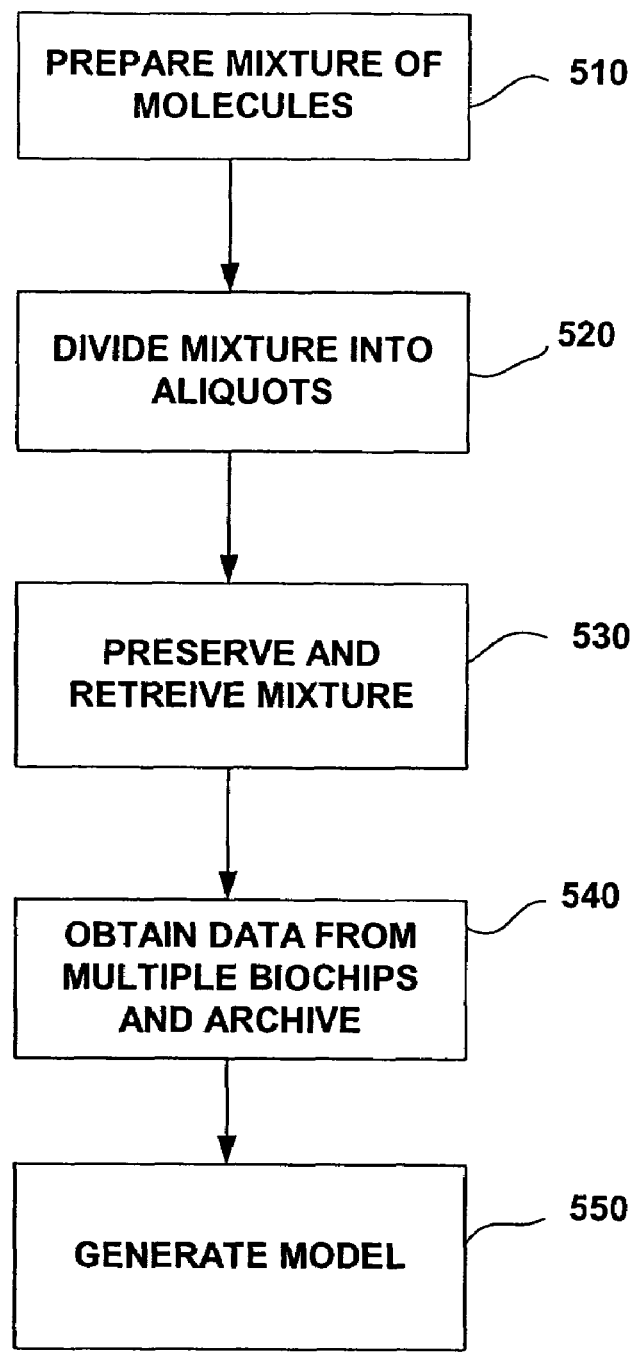
FIG. 5 depicts a method of generating a model for distinguishing between types of biochips according to an aspect to the invention.

A method of generating a model for classifying biochip type is shown generally in FIG. 5. As an initial step, a mixture of molecules is generated at a step 510. The mixture of molecules may be similar to that used to generate the model described above. The mixture of molecules is divided into aliquots at a step 520. The aliquots may then be preserved and retrieved at a step 530 in a manner similar to the method described in reference to FIG. 1. The mixture is then analyzed at a step 540 to obtain mass spectral data. The data obtained are then archived with respect to chip type. The data obtained from the group of biochips may then be input into the KDE at a step 550 to obtain a general biochip model. The KDE may extract only those features that are salient to distinguishing one biochip surface from another.

In general, the KDE will search for hidden or subtle patterns of molecular expression that are, in and of themselves, "diagnostic." The level of the identified molecular products is termed per se diagnostic, because the level of the product is diagnostic without any further consideration of the level of any other molecular products in the sample. In some instances, a normalizing molecular product may be used to normalize the level of the molecular products. The data may be normalized internally within the features in a vector. Alternatively, a synthetic peptide or other high molecular weight molecule may be added as an internal standard.

In the data cluster analysis utilizing the KDE, the diagnostic significance of the level of any particular marker, e.g., a protein or transcript, is a function of the levels of the other elements that are used to calculate a sample vector. Such products are referred to as "contextual diagnostic products." The KDE's learning algorithm discovers wholly new classification patterns without knowing any prior information about the identity or relationships of the data pattern, i.e., without prior input that a specified diagnostic molecular product is indicative of a particular classification.

As used in one method of the invention, data from each of the mass spectra are input into the KDE. The KDE then seeks to identify clusters of data (hidden patterns) in n-dimensional space, where n is the number of mass to charge values from the spectra, and each spectrum can be mapped into the n-dimensional space using the magnitude of each of the selected mass to charge values in the spectrum. The KDE seeks clusters that are contain as many of the vectors as possible and that distinguish each of the biochips from the others.

After the model is generated, new biochips may be obtained, for example, from a newly manufactured batch of biochips. A method of classifying and identifying particular types of biochips is illustrated generally as FIG. 6. Once new biochips are obtained in step 600, it may be desirable to determine if the biochips satisfy predetermined standards for quality.

A number of biochips may be selected from the new group of biochips, and data obtained on the selected biochips at step a 610. To obtain data on the new biochip, an aliquot of the preserved mixture of molecules is retrieved. To ensure an accurate characterization, the molecular mixture to be used is as similar as possible, and preferably identical, to the original mixture used to construct the models. The data may be obtained using mass spectrometry.

Once data have been obtained on the selected biochip, the data are mapped in n-dimensional space to the model in a step 620. After the data is mapped to the model, a determination is made in a step 630 of whether the data maps to an archived biochip. If the data obtained from the mass spectrometry map to an archived biochip, the biochip being tested can be classified as the archived biochip in a step 631.

If the data do not map to an archived biochip, a determination is made in a step 640 of whether the data map consistently to a new cluster. If the data do map to a new cluster, the conclusion is reached in a step 641 that the biochip is of a new biochip type, and the biochip may be archived in a step 642.

If the data do not map to a new cluster, the data may map to a number of unrelated clusters in a step 650. If this is the case, the conclusion is reached in a step 660 that the batch of new biochips may be substandard, and a new batch should be obtained.

While the foregoing example was discussed with respect to a method of quality assurance/quality control for a SELDI- or other MALDI-type system, the methods of the invention are equally applicable to electrospray systems as well. For example, rather than distinguishing between chip surfaces, the method when employed using electrospray is capable of distinguishing between different diluents or diluent concentrations.

A method for distinguishing between different types of diluent according to one aspect of the invention will now be described. Preparation, preservation, and retrieval of the mixture of molecules will be substantially the same as that described above with respect to biochips.

One particular difference is in the means of obtaining data from the molecular mixture. Using the electrospray system in conjunction with a mass spectrometer, mass spectral data is obtained. In order to obtain data using an electrospray, the mixture of molecules is combined with a diluent to achieve a predetermined concentration. Thus, the resultant spectral information will include information specific to the mixture of molecules, as well as spectral information specific to the diluent used. Therefore, rather than obtaining spectral data from multiple biochips and archiving the biochips, as illustrated in FIG. 5, step 540, one may obtain spectral data from multiple diluents and archive the diluents.

Figure 6:
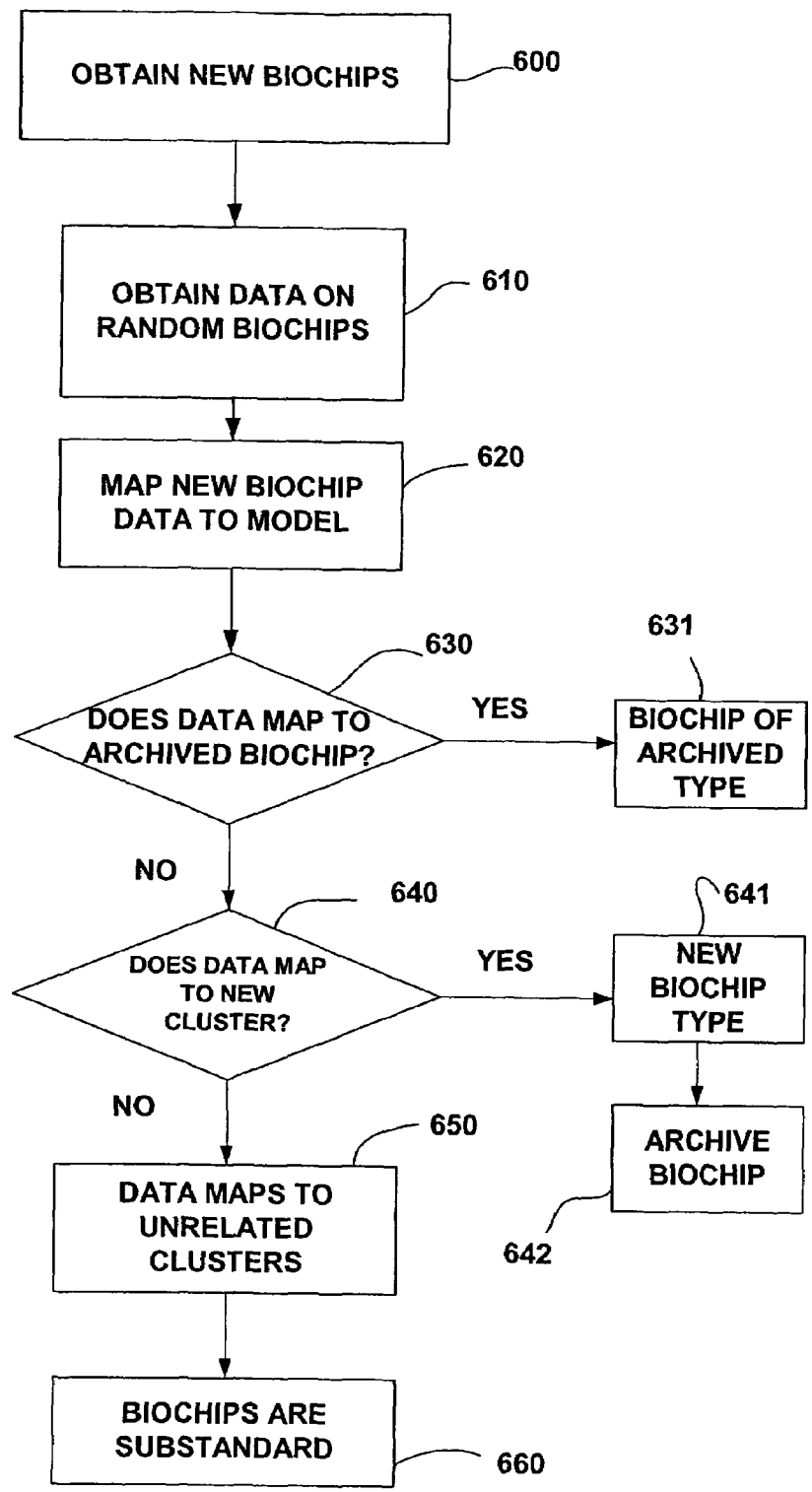
FIG. 6 illustrates a method of comparing a new batch of biochips to an archive of biochips to classify types of biochips.

Another difference between the method of distinguishing between biochips and diluents includes obtaining new diluents, rather than obtaining new biochips, as illustrated in FIG. 6, 600. Additionally, rather than selecting random biochips, as shown in FIG. 6, 610, multiple samples of diluent may be used.

The method illustrated in FIG. 6 may be employed as illustrated. Using the method illustrated in FIG. 6 as applied to electrospray technology, diluents may be monitored for quality. If, for example, the data from the new diluent maps to a number of unrelated clusters, then the diluent may be substandard and a new diluent should be prepared.

While molecules disclosed had a molecular weight of greater than 400, other molecules having molecular weights acceptable for use in bioassay processes will be apparent to those skilled in the art based on the teachings provided herein.

As described above, preserving the aliquots was performed by freezing the aliquots using liquid nitrogen. The use of other cryogenic and non-cryogenic preservation methods are intended to be within the scope of the invention.

Additionally, one method of determining the distance between a test centroid and a control centroid is illustrated above for Cartesian systems. Other methods for calculating the distance between a control centroid and a test centroid are known in the art and are within the scope of the present invention. Some specific methods of calculating distance include Euclidian distance calculations, Hamming distance calculations, and Mahalanobis distance calculations The various features of the invention have been described in relation to a method of quality assurance/quality control of high-throughput bioassay processes. However, it will be appreciated that many of the steps may be implemented with various apparatus and bioinformatics methods. Moreover, variations and modifications exist that would not depart from the scope of the invention.

We claim:

1. A method of evaluating the results from a bioassay process, the method comprising:
   preparing a mixture of molecules;
   dividing the mixture of molecules into a plurality of aliquots;
   preserving the plurality of aliquots;
   retrieving a first aliquot, the first aliquot being a control aliquot;
   obtaining data from the control aliquot using the bioassay process, the data including values for n features, which collectively define a control centroid in an n-dimensional space;
   subsequently retrieving a second aliquot, the second aliquot being a test aliquot;
   obtaining data from the test aliquot using the bioassay process, the data including values for the n features, which collectively define a test centroid in the n-dimensional space; and determining whether the displacement in the n-dimensional space of the test centroid exceeds a predetermined distance from the control centroid as an indication of whether the bioassay has generated unreliable results.

2. The method of claim 1, wherein the obtaining data from the control aliquot using the bioassay process includes using an electrospray process.

3. The method of claim 1, wherein the obtaining data from the control aliquot using the bioassay process includes using a biochip.

4. The method of claim 1, wherein the obtaining data from the control aliquot includes:
selecting a subset of n features from a plurality of features associated with the control aliquot.

5. The method of claim 1, wherein each feature is a mass-to-charge ratio and the value of each feature is a magnitude.

6. The method of claim 1, wherein the retrieving a first aliquot includes retrieving two or more aliquots.

7. A method of evaluating the results from a bioassay process, comprising:
retrieving a test aliquot of a preserved molecular mixture;
analyzing data from the test aliquot using a bioassay process;
comparing a test set of features of the test aliquot with a control set of features based on a control aliquot from the preserved molecular mixture, the control set of features defining a control centroid in an n-dimensional space, the test set of features defining a test centroid in the n-dimensional space, the test set of features of the retrieved mixture being the same as the control set of features; and
determining whether the position of the test centroid is greater than a predetermined displacement from the control centroid as an indication of whether the bioassay has generated unreliable results.

8. The method of claim 7, wherein said features are mass-to-charge ratios and wherein said comparing includes comparing magnitudes of each of the test set of mass-to-charge ratios with the magnitudes of the control set of mass-to-charge ratios.

9. The method of claim 7, wherein the analyzing data from the test aliquot using a bioassay process includes analyzing data from the test aliquot using an electrospray process.

10. The method of claim 7, wherein the analyzing data from the test aliquot using a bioassay process includes analyzing data from the test aliquot using a biochip.

11. The method of claim 7, wherein the predetermined displacement is two standard deviations.

12. A method for evaluating the results from a bioassay that generates spectral data, comprising:
providing a location in an n-dimensional space of a control centroid associated with control spectral data generated from a first aliquot of a prepared mixture of molecules;
generating test spectral data from a second aliquot of the mixture;
computing a location in the n-dimensional space of a test centroid associated with the test spectral data;
comparing the test centroid to the control centroid to determine the displacement in n-dimensional space of the test centroid from the control centroid; and
determining whether the test centroid is greater than a predetermined displacement from the control centroid as an indication of whether the bioassay has generated unreliable results.

13. The method of claim 12, wherein the mixture of molecules includes a mixture of isolated peptides.

14. The method of claim 12, wherein the mixture of molecules includes molecules that are water soluble and have a molecular weight greater than 400.

15. The method of claim 12, wherein the bioassay includes an electrospray process.

16. The method of claim 12, wherein the bioassay includes a biochip-based process.

17. The method of claim 12, wherein the determining whether the test centroid is within a predetermined distance includes one of: determining that the bioassay process is functioning properly when the test centroid is within or is equal to the predetermined distance from the control centroid, and determining that the bioassay process is not functioning properly when the test centroid is beyond the predetermined distance from the control centroid.

18. The method of claim 12, wherein each of the features is a mass-to-charge ratio.

19. The method of claim 12, wherein the mixture of molecules is a biological sample.

20. The method of claim 12, wherein the spectral data are generated by a mass spectrometer.

21. The method of claim 12, further comprising repeating the generating test spectral data and computing a location for multiple aliquots of the mixture of molecules over time to monitor performance of the bioassay.

22. The method of claim 12, wherein the mixture of molecules is selected from the group consisting of naturally-occurring and non-naturally-occurring molecules.

23. A method for evaluating the results from a bioassay that generates spectral data, comprising:
providing a location in an n-dimensional space of a control centroid associated with control spectral data generated from a first aliquot of a prepared mixture of molecules;
providing a location in an n-dimensional space of a test centroid associated with test spectral data generated from a second aliquot of the prepared mixture of molecules;
comparing the test centroid to the control centroid to determine the displacement in n-dimensional space of the test centroid from the control centroid; and
determining whether the displacement in n-dimensional space of the test centroid exceeds a predetermined distance from the control centroid, wherein the determining whether the displacement in n-dimensional space of the test centroid exceeds a predetermined distance from the control centroid includes one of: indicating to a user that the bioassay process is functioning properly when the test centroid is within or is equal to the predetermined distance from the control centroid, and indicating to a user that the bioassay process is not functioning properly when the test centroid is beyond the predetermined distance from the control centroid.

* * * * *

UNITED STATES PATENT AND TRADEMARK OFFICE
CERTIFICATE OF CORRECTION

PATENT NO. : 7,333,895 B2
APPLICATION NO. : 10/628135
DATED : July 28, 2003
INVENTOR(S) : Ben A. Hitt et al.

It is certified that error appears in the above-identified patent and that said Letters Patent is hereby corrected as shown below:

Column 2, line 2, replace "Soft-ware" with -- Software --.

Column 3, line 59, after "spectra." Add the following:

[The centroid is a point identifying the center of all the vectors associated with the chosen features in n-dimensional space.]

Signed and Sealed this

Twenty-seventh Day of January, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,333,895 B2 Page 1 of 1
APPLICATION NO. : 10/628135
DATED : February 19, 2008
INVENTOR(S) : Ben A. Hitt et al.

It is certified that error appears in the above-identified patent and that said Letters Patent is hereby corrected as shown below:

Column 2, line 2, replace "Soft-ware" with -- Software --.

Column 3, line 59, after "spectra." Add the following:

[The centroid is a point identifying the center of all the vectors associated with the chosen features in n-dimensional space.]

This certificate supersedes the Certificate of Correction issued January 27, 2009.

Signed and Sealed this

Seventeenth Day of February, 2009

JOHN DOLL
*Acting Director of the United States Patent and Trademark Office*